US008124363B2

(12) United States Patent (10) Patent No.: US 8,124,363 B2
Weart et al. (45) Date of Patent: Feb. 28, 2012

(54) DETECTION OF *TRICHOMONAS*

(75) Inventors: Ilona F. Weart, Woodstock, GA (US); Shu-Paing Yang, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 394 days.

(21) Appl. No.: 12/419,361

(22) Filed: Apr. 7, 2009

(65) Prior Publication Data

US 2009/0226941 A1 Sep. 10, 2009

Related U.S. Application Data

(62) Division of application No. 10/972,140, filed on Oct. 22, 2004, now Pat. No. 7,514,230.

(51) Int. Cl.
*G01N 33/53* (2006.01)
*G01N 33/569* (2006.01)
(52) U.S. Cl. ...................................... 435/7.22
(58) Field of Classification Search .................. 435/7.22
See application file for complete search history.

(56) References Cited

U.S. PATENT DOCUMENTS

| | | | |
|---|---|---|---|
| 5,585,273 A | 12/1996 | Lawrence | |
| 6,117,090 A | 9/2000 | Caillouette | |
| 6,251,660 B1 | 6/2001 | Muir et al. | |
| 6,426,227 B1 | 7/2002 | Kritzman et al. | |
| 7,094,528 B2 | 8/2006 | Song et al. | |

FOREIGN PATENT DOCUMENTS

| | | |
|---|---|---|
| EP | 1422525 A1 | 5/2004 |
| WO | WO 9615255 A2 | 5/1996 |
| WO | WO 0065347 A2 | 11/2000 |
| WO | WO 0065348 A2 | 11/2000 |
| WO | WO 2006046990 A1 | 5/2006 |

OTHER PUBLICATIONS

Communication Relating to the Results of the Partial International Search in corresponding PCT Application No. PCT/US20051026720, Nov. 2, 2005, 4 pages.
Ackers, J. P., Chapter 4. *Immunologic Aspects of Human Trichomoniasis, In: Trichomonads Parasitic in Humans*, Honigberg, B. M., Editor, Springer-Verlag New York, Inc., (1989), pp. 36-52.
Addis, Maria F., et al., *Cloning and Molecular Characterization of a cDNA Clone Coding for Trichomonas vaginalis Alpha-Actinin and Intracellular Localization of the Protein*, Infection and Immunity, 66 (10), (1998), pp. 4924-4931.
Alderete, John F., et al., *Iron Mediates Trichomonas vaginalis Resistance to Complement Lysis*, Microbial Pathogenesis, 19 (2), (1995), pp. 93-103.
Alderete, J. F., et al., *The Vagina Has Reducing Environment Sufficient for Activation of Trichomonas vaginalis Cysteine Proteinases*, Genitourinary Medicine, 73, (1997), pp. 291-296.
Alderete, J. F., et al., *The Vagina of Women Infected With Trichomonas vaginalis has Numerous Proteinases and Antibody to Trichomonad Proteinases*, Genitourinary Medicine, 67 (6), (1991), pp. 469-474.

Alvarez-Sanchez, Maria E., et al., *A Novel Cysteine Proteinase (CP65) of Trichomonas vaginalis Involved in Cytotoxicity*, Microbial Pathogenesis, 28 (4), (1999),pp. 193-202.
Arroyo, Rossana, et al., *Two Trichomonas vaginalis Surface Proteinases Bind to Host Epithelial Cells and Are Related to Levels of Cytoadherence and Cytotoxicity*, Archives of Medical Research, 26 (3), (1995), pp. 279-285.
Bózner, P., *Proteinases in Trichomonas vaginalis and Tritrichomonas mobilensis are Not Exclusively of Cystein Type*, Parasitology, 102 (1), (Feb. 1991), pp. 113-115.
Cappuccinelli, Piero, et al., *Structural and Molecular Organization of Trichomonas vaginalis Cytoskeleton*, Acta Universitatis Carolinae—Biologica, 30 (Part 1), Trichomonads and Trichomoniasis—Proceedings of the International Symposium held in Prague, Czechoslovakia, Jul. 3-7, 1985, (1987), pp. 211-217.
Chen, Hsiuchen, et al., *A New Signal Sequence Trap Using Alkaline Phosphates as a Report*, Nucleic Acids Research, 27 (4), (1999), pp. 1219-1222.
Chubb, Anthony J., et al., *Identification of Mycobacterium tuberculosis Signal Sequences That Direct the Export of a Leaderless β-Lactamase Gene Product in Escherichia coli*, Microbiology, 144 (6), (1998), pp. 1619-1629.
Costa E Silva Filho, Fernando, et al., *Trichomonas vaginalis and Tritrichomonas foetus secrete neuraminidase into the Culture Medium*, Molecular and Biochemical Parasitology, 35 (1), (1989), pp. 73-78.
Draper, Deborah, et al., *Cysteine Proteases of Trichomonas vaginalis Degrade Secretory Leukocyte Protease Inhibitor*, Journal of Infectious Diseases, 178 (3), (1998), pp. 815-819.
Garber, Gary E., et al., *Analysis of the Extracellular Proteases of Trichomonas vaginalis*, Parasitology Research, 80 (5), (1994), pp. 361-365.
Garber, Gary E., et al., *Isolation of a Cell-Detaching Factor of Trichomonas vaginalis*, Journal of Clinical Microbiology, 27, (1989), pp. 1548-1553.
Hernandez-Gutierrez, Rodolfo, et al., *A 39-kDa Cysteine Proteinase CP39 From Trichomonas vaginalis, Which Is Negatively Affected by Iron May Be Involved in Trichomonal Cytotoxicity*, The Journal of Eukaryotic Microbiology, 50 (Supp), (2003), pp. 696-698.
Irvine, Joseph W., et al., *Purification of Cysteine Proteinases From Trichomonads Using Bacitracin-Sepharose*, FEBS Microbiology Letters, 110, (1993), pp. 113-120.
Irvine, Joseph W., et al., *Use of Inhibitors to Identify Essential Cysteine Proteinases of Trichomonas vaginalis*, FEMS Microbiology Letters, 149 (1), (1997), pp. 45-50.
Krieger, John N., *Geographic Variation Among Isolates of Trichomonas vaginalis: Demonstration of Antigenic Heterogeneity by Using Monoclonal Antibodies and the Indirect Immunofluorescence Technique*, The Journal of Infectious Diseases 152 (5), (1985), pp. 979-984.
Krieger, John N., *Urologic Aspects of Trichomoniasis*, Investigative Urology, 13 (5), (1981), pp. 411-417.
Laga, Marie, et al., *Non-Ulcerative Sexually Transmitted Diseases at Risk Factors for HIV-1 Transmission in Women: Results From a Cohort Study*, AIDS, 7, (1993), pp. 95-102.
León-Sicairos, Claudia R., et al., *tvcp12: A Novel Trichomonas vaginalis Cathepsin L-Like Cysterine Proteinase-Encoding Gene*, Microbiology, 150 (5), (2004), pp. 1131-1138.
León-Sicairos, Claudia Del Rosario, et al., *Two Trichomonas vaginalis Loci Encoding for Distinct Cysteine Proteinases Show a Genomic Linkage With Putative Inositol Hexakisphosphate Kinase (IP6K2) or an ABC Transporter Gene*, Journal of Eukaryotic Microbiology, 50 (Supp), (2003), pp. 702-705.

(Continued)

*Primary Examiner* — Gary Nickol
*Assistant Examiner* — Nina Archie
(74) *Attorney, Agent, or Firm* — Dority & Manning, P.A.

(57) ABSTRACT

The present invention is directed to diagnostic devices and methods for detecting *Trichomonas* infections.

9 Claims, 2 Drawing Sheets

OTHER PUBLICATIONS

Lisi, Peter J., et al., *Monoclonal-Antibody-Based Enzyme-Linked Immunosorbent Assay for Trichomonas vaginalis*, Journal of Clinical Microbiology, 26 (9), (1988), pp. 1684-1686.

Lubick, Kirk J., et al., *Purification and Analysis of a Phospholipase A2-Like Lytic Factor of Trichomonas vaginalis*, Infection and Immunity, 72 (3), (Mar. 2004), pp. 1284-1290.

Mallinson, David J., et al., *Identification and Molecular Cloning of Four Cysteine Proteinase Genes From the Pathogenic Protozoon Trichomonas vaginalis*, Microbiology, 140 (10), (1994), pp. 2725-2735.

McGregor, James A., et al., *Association of Cervicovaginal Infections With Increased Vaginal Fluid Phospholipase $A_2$ Activity*, American Journal of Obstetrics and Gynecology, 167 (6), (1992), pp. 1588-1594.

Mendoza-Lopez, M. R., et al., *CP30, a Cysteine Proteinase Involved in Trichomonas vaginalis Cytoadherence*, Infection and Immunity, 68 (9), (2000), pp. 4907-4912.

Min, Duk-Young, et al., *Degradations of Human Immunoglobulins and Hemoglobin by a 60 kDa Cysteine Proteinase of Trichomonas vaginalis*, The Korean Journal of Parasitology, 36 (4), (Dec. 1998), pp. 261-268.

Moore, John T., et al., *The Development of β-Lactamase as a Highly Versatile Genetic Reporter of Eukaryotic Cells*, Analytical Biochemistry, 247, (1997), pp. 203-209.

Moskowitz, Mitchell O., et al., *Sexually Transmitted Diseases and Their Relation to Male Infertility*, The Urologic Clinics of North America, 19 (1), (1992), pp. 35-45.

North, M J., et al., *The Specificity of Trichomonad Cysteine Proteinases Analysed Using Fluorogenic Substrates and specific inhibitors*, Molecular and Biochemical Parasitology, 39 (2), (Mar. 1990), pp. 183-193.

Provenzano, Daniele, et al., *Analysis of Human Immunoglobulin-Degrading Cysteine Proteinases of Trichomonas vaginalis*, Infection and Immunity, 63 (9), (1995), pp. 3388-3395.

Raz, Erez, et al., *β-Lactamase as a Marker for Gene Expression in Live Zebrafish Embryos*, Developmental Biology, 203, (1998), pp. 290-294.

Thomason, J. L., et al., *Trichomonas vaginalis*, Obstetrics and Gynecology, 74 (3), (Part 2), (1989), pp. 536-541.

Vargas-Villarreal, Javier, et al., *Trichomonas vaginalis: Identification of a Phospholipase A-Dependent Hemolytic Activity in a Vesicular Subcellular Fraction*, The Journal of Parasitology, 89 (1), (2003), pp. 105-112.

Wasserheit, Judith N., *Epidemiological Synergy—Interrelationships Between Human Immunodeficiency Virus Infection and Other Sexually Transmitted Diseases*, Sexually Transmitted Diseases, 19 (2), (Mar.-Apr. 1992), pp. 61-77.

Zhang, Zuo-Feng, et al., *Is Trichomonas vaginalis a Cause of Cervical Neoplasia? Results From a Combined Analysis of 24 Studies*, International Journal of Epidemiology, 23 (4), (1994), pp. 682-690.

Zlokarnik, Gregor, et al., *Quantitation of Transcription and Clonal Selection of Single Living Cells With β-Lactamase as Reporter*, Science, 279 (5347), (Jan. 2, 1998), pp, 84-88.

DETECTION OF TRICHOMONAS

RELATED APPLICATIONS

The present application is a divisional of U.S. application Ser. No. 10/972,140, filed on Oct. 22, 2004, which is incorporated herein in its entirety by reference thereto.

FIELD OF THE INVENTION

The invention relates to diagnostic devices and methods for detecting *Trichomonas* infections.

BACKGROUND OF THE INVENTION

*Trichomonas vaginalis* is the cause one of the most widespread sexually transmitted diseases in the world. The main pathological manifestations of a trichomonad infection in women are abdominal pain, itching, and presence of a foul-smelling discharge with abundant leukocytes Honigberg, B. M. 1978. Trichomonads of importance in human medicine, p. 275. In J. P. Kreier (ed.), Parasitic protozoa, vol. II. Academic Press, Inc., New York, N.Y. In men, the infection is mostly asymptomatic, although it can sometimes lead to urethritis, prostatitis, and epididymitis. Krieger, J. N. 1981. Urologic aspects of trichomoniasis. Investig. Urol. 18:411-417. The infection recently has been associated with severe complications, including infertility. Moskowitz, M. O., and B. C. Mellinger. 1992. Sexually transmitted diseases and their relation to male infertility. Urol. Clin. North Am. 19:35-45. *Trichomonas* infection also gives rise to an enhanced predisposition to neoplastic transformation in cervical tissues, and progression of human immunodeficiency virus. Zhang, Z. F., and C. B. Begg. 1994. Is *Trichomonas vaginalis* a cause of cervical neoplasia? Results from a combined analysis of 24 studies. Int. J. Epidemiol. 23:682-690; Laga, M., A. Manoka, M. Kivuvu, B. Malele, M. Tuliza, N. Nzila, J. Goeman, F. Behets, V. Batter, M. Alary, W. L. Heyward, R. W. Ryder, and P. Piot. 1993. Non-ulcerative sexually transmitted diseases as risk factors for HIV-1 transmission in women: results from a cohort study. AIDS 7:95-102; Wasserheit, J. N. 1992. Interrelationship between human immunodeficiency virus infection and other sexually transmitted diseases. Sex. Transm. Dis. 19:61-77.

*T. vaginalis* can survive and flourish in a hostile changing environment. Its ability to evade the host immune system is an important aspect of its pathogenesis. Avoidance of complement is a strategic tactic which is used by *T. vaginalis* to overcome the human immune system. It is known that *T. vaginalis* activates an alternative pathway of complement but workers are only just beginning to understand how the parasite does this and how it escapes eradication. It is known that *T. vaginalis* takes advantage of a niche in which little complement is present. Cervical mucus is surprisingly deficient in complement. Menstrual blood represents the only source of complement available to the vagina. Interestingly, its complement activity is about half that of venous blood, and about one-third of menstrual blood samples have no complement activity at all. Menstrual blood has appreciable complement-mediated cytotoxicity toward *T. vaginalis*, and although a reduction in parasite concentration is seen during menses, trichomonal infection persists even after menses. While the number of organisms in the vagina actually decreases during menses, virulence factors, many of which are mediated by iron, contribute to the exacerbation of symptoms at this time.

Iron is a contributing factor in complement resistance by *T. vaginalis*. It appears that iron up-regulates the expression of CPs, which have been found to degrade the C3 portion of complement on the surface of the organism and that this mechanism allows the organism to evade complement-mediated destruction. Alderete, J. F., D. Provenzano, and W. Lehker. 1995. Iron mediates *Trichomonas vaginalis* resistance to complement lysis. Microb. Pathog. 19:93-103.

Current methods for detecting and diagnosing *Trichomonas* infection involve a trip to a clinic or doctor's office. However, given the prevalence of *Trichomonas* infections and their potential harm, faster, simpler methods for detecting *Trichomonas* infections are needed. In particular, a diagnostic device is needed that can be used outside of a clinical setting, for example, in the home or in the field.

SUMMARY OF THE INVENTION

The invention is directed to diagnostic devises and methods for detecting *Trichomonas* infections.

One aspect of the invention is a diagnostic device that includes a core and a multitude of reporter enzymes, wherein each reporter enzyme is directly or indirectly linked to the core by a linker, and wherein the linker can be cleaved by a *Trichomonas*-specific enzyme after insertion of the device in a mammalian vagina. The core can be surrounded by membrane to which the reporter enzymes are linked. The reporter enzymes can be present in one zone of the core (this may facilitate detection of the infection). The *Trichomonas*-specific enzyme can be a *Trichomonas vaginalis* enzyme or a *Trichomonas foetus* enzyme. The enzymes can be proteinases, phospholipase A2-like lytic enzymes, or neuraminidases. In some embodiments, the reporter enzymes are cysteine proteinases. The enzymes can be proteinases that cleave a linker with a cleavage site that includes Arg-Arg, Phe-Arg, Val-Leu-Lys, Ala-Phe-Lys, Pro-Phe-Arg, or Leu-Val-Tyr. In another embodiment, the reporter enzymes are phospholipase A2-like enzymes. Such phospholipase A2-like enzymes can cleave a linker with a cleavage site that includes a phosphoglyceride. The phospholipase A2-like enzymes can also cleave an alkylene linker with a cleavage site comprising:

X—CH$_2$—O—CO-alkylene wherein X is a alkylene or triglyceride. In another embodiment, the reporter enzymes are neuraminidases. Such neuraminidases can cleave a linker with a cleavage site that includes an alpha-D-N-acetylneuramic acid.

Another aspect of the invention is a kit that includes (a) a diagnostic device of the invention that comprises a core and a multitude of reporter enzymes, each reporter enzyme linked directly or indirectly to the core by a linker, and (b) an indicator for detecting the reporting enzymes, wherein the linker can be cleaved by a *Trichomonas*-specific enzyme after insertion of the device in a mammalian vagina. The indicator can include a substrate for the reporter enzymes, for example, where the substrate gives rise to a colored product after cleavage by the reporter enzymes.

Another aspect of the invention is a method for detecting *Trichomonas* in a vagina of a female mammal that includes inserting a diagnostic device into a test subject's vagina, retaining the device in the vagina for a time sufficient for reaction of an infective agent with reporter enzymes on the device, removing the device and dipping the device into a solution containing an indicator to detect whether *Trichomonas* is in a vagina of a female mammal.

Another aspect of the invention includes a diagnostic device that includes a (1) a core; (2) a multitude of primary antibodies and (3) a compartment containing secondary antibodies for detecting a complex formed between the primary antibodies and one or more *Trichomonas* surface antigens; wherein the primary antibodies can bind to one or more of the *Trichomonas* surface antigens and each primary antibody is linked directly or indirectly to the core. The compartment of the device can also contain a fluid in which the secondary antibodies are suspended. Such a compartment can be ruptured when squeezed. The primary antibodies and the secondary antibodies of the device can bind to the same or to different *Trichomonas* surface antigens. In some embodiments, the secondary antibodies are conjugated to a detectable label. The core of the device can be surrounded by a membrane to which the primary antibodies are linked. In some embodiments, the primary antibodies are immobilized onto a zone of the core. The *Trichomonas* surface antigens can be *Trichomonas vaginalis* surface antigens or *Trichomonas foetus* surface antigens. Examples of *Trichomonas* surface antigens include tubulin antigens or actin antigens from *Trichomonas* species. The *Trichomonas* surface antigens can also be alpha-actinin polypeptides, for example, those with SEQ ID NO:2.

Another aspect of the invention is a kit that includes: (a) device that comprises (1) a core; (2) a multitude of primary antibodies and (3) a compartment containing secondary antibodies for detecting a complex formed between the primary antibodies and one or more *Trichomonas* surface antigens; wherein the primary antibodies can bind to one or more of the *Trichomonas* surface antigens and each primary antibody is linked directly or indirectly to the core; and (b) instructions for using the device. The kit can also include a container containing an indicator solution for detecting the secondary antibodies.

Another aspect of the invention is a method for detecting *Trichomonas* in a vagina of a female mammal that includes inserting a diagnostic device into a test subject's vagina, retaining the device in the vagina for a time sufficient for reaction of antigens on an infective agent (e.g., *Trichomonas*) with primary antibodies on the device, removing the device from the vagina, squeezing a compartment in the device to release secondary antibodies in the compartment and detecting whether *Trichomonas* is present in a vagina of the female mammal. The device can be washed in a convenient fluid such as water after squeezing the compartment. In some embodiments, the device is washed in water after allowing sufficient time for the secondary antibodies from the compartment to bind to the antigens.

DETAILED DESCRIPTION OF THE INVENTION

Figure 1:
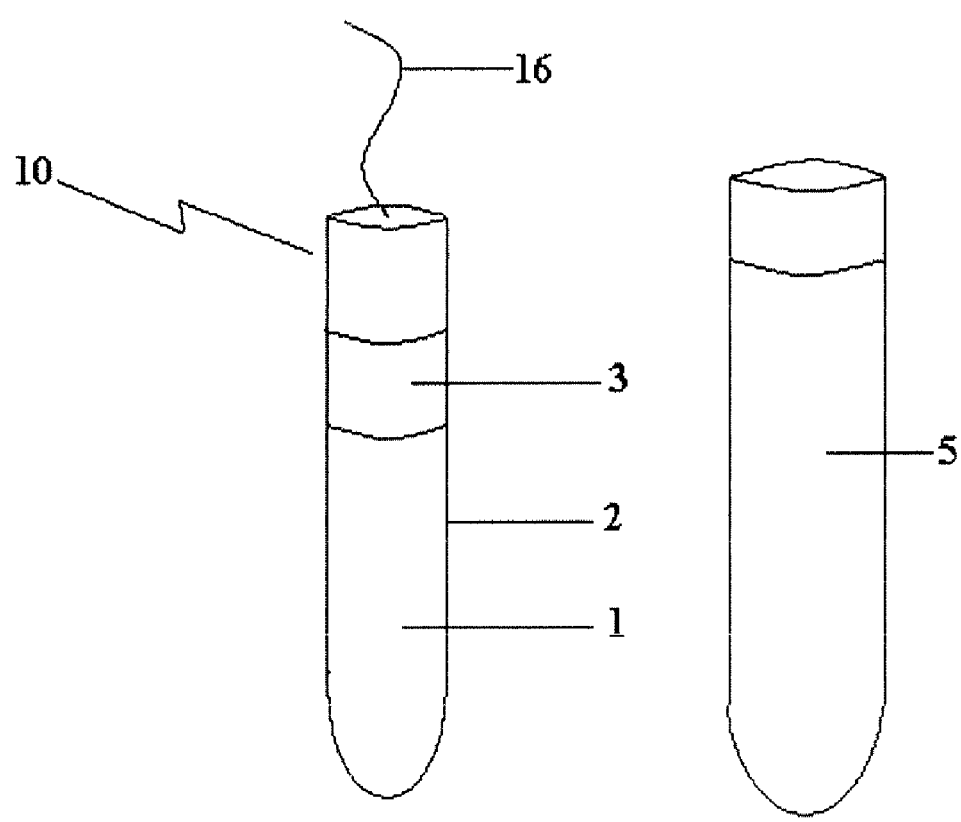
FIG. 1 provides a diagnostic device and a color reaction vessel for detecting an enzyme specific to an infective agent such as *Trichomonas*. The device has a core (1); and reporter enzymes (3), i.e. signal generating enzymes, which are linked to the core (1) or to a membrane (2) surrounding the core (1) by a linker that can be cleaved by an enzyme specific to the infective agent. In some embodiments, the reporter enzymes (3) are present in one zone of the core (1); in other embodiments, the reporter enzymes (3) coat the surface of the core (1) or the surface of the membrane surrounding the core (1). After insertion of the diagnostic device into a test subject's vagina, the device is retained in the vagina for a time sufficient for reaction of an infective agent (or an enzyme specific to the infective agent) with the reporter enzymes (3). The device is then removed, dipped several times in a solution containing a color indicator (5) and then removed and discarded. The color indicator (5) can change color, or develop color, in the presence of the reporter enzymes (3). Hence, if the infective agent is present, some of the reporter enzymes (3) will be cleaved from the absorbent core (I) and be washed into the color indicator (5) solution where the liberated reporter enzymes will cause the color indicator (5) to change color, or to develop a colored solution.

The invention relates to diagnostic devices and methods for detecting vaginal infections, for example, *Trichomonas* infections. The diagnostic devices of the invention include a vaginal insert or tampon having a solid support core material with at least one antibody specific for an antigen of an infective agent or at least one reporter enzyme attached to the core material or to a membrane covering the core material. The reporter enzyme is attached to the core or membrane by a linker that can be cleaved by an enzyme specific to an infective agent. The infective agent-specific antibodies or reporter enzymes can also be bound to and be within the material of the solid support core. The methods of the invention involve inserting a diagnostic device of the invention into a female mammal's vagina for a time sufficient to permit binding of infective agent-specific antigens or interaction of the reporter enzymes with the infective agent-specific enzyme. The diagnostic device can then be removed and the presence of infective agent-specific antigens or enzymes can then be detected. The presence of infective agent-specific antigens or enzymes can be detected by use of a color indicator (5) that changes color when the complex between the antibodies and the infective agent-specific antigen forms or when a product forms from a reaction between the reporter enzyme and the color indicator (5). In some embodiments, the color indicator (5) can react with the secondary antibodies (15) to generate a new color or signal.

*Trichomonas*

In some embodiments, the infective agent detected by the devices of the invention is *Trichomonas*. *Trichomonas vagi-*

*nalis* is a flagellated protozoan parasite possessing five flagella, four of which are located at its anterior portion. The fifth flagellum is incorporated within the undulating membrane of the parasite, which is supported by a slender non-contractile costa. The flagella and the undulating membrane give this parasite a characteristic quivering motility. Under unfavorable growth conditions, *T. vaginalis* can round up and internalize the flagella. Some workers believe these forms to be pseudocysts, but it is more likely that they are degenerate forms of *T. vaginalis*, since they have not been reported to give rise to normal motile forms.

*Trichomonas*-Specific Antibodies

Any available *Trichomonas*-specific antibody can be used in the present devices and methods for detecting *Trichomonas* infection.

For example, two broadly reactive monoclonal antibodies are available that identify all 88 strains of *T. vaginalis* obtained from diverse geographic areas of North America. See, Krieger, J. N., K. K. Holmes, M. R. Spence, M. F. Rein, W. M. McCormack, and M. R. Tam. 1985. Geographic variation among isolates of *Trichomonas vaginalis*: demonstration of antigenic heterogeneity by using monoclonal antibodies and the indirect immunofluorescence technique. J. Infect. Dis. 152:979-984.

Monoclonal antibodies to 62-kDa and 65-kDa *T. vaginalis* proteins are also available that permit detection of *T. vaginalis* in clinical specimens. See, Lisi, P. J., R. S. Dondero, D. Kwiatkoski, M. R. Spence, M. F. Rein, and J. F. Alderete. 1988. Monoclonal-antibody-based enzyme-linked immunosorbent assay for *Trichomonas vaginalis*. J. Clin. Microbiol. 26:1684-1686.

Moreover, monoclonal antibodies to proteins such as cell-detaching factor (CDF; 200 kDa) and cysteine protease (60 kDa), which are immunogens observed in all the isolates of *T. vaginalis*, are also available for detection of trichomoniasis. For example, a *Trichomonas* Direct Enzyme Immunoassay and Fluorescent Direct Immunoassay (California Integrated Diagnostics, Benicia, Calif.), has peroxidase-labeled and fluorophore-labeled cocktails of monoclonal antibodies to various *T. vaginalis* structures. See, Thomason, J. L., and S. M. Gelbert. 1989. *Trichomonas vaginalis*. Obstet. Gynecol. 74:536-541.

Any one or any combination of these *Trichomonas*-specific antibody preparations can be used in the devices and methods of the invention.

*Trichomonas*-Specific Antigens

A number of *Trichomonas*-specific antigens have been identified that can be used for developing antibodies that bind with specificity to *Trichomonas*.

For example, the cytoskeleton of *T. vaginalis* is composed of tubulin and actin fibers. Monoclonal antibodies to these tubulin and actin molecules are available. See, e.g., Cappuccinelli, P., C. Sellitto, D. Zicconi, and C. Juliano. 1987. Structural and molecular organization of *Trichomonas vaginalis* cytoskeleton. Acta Univ. Carol. Biol. 30(314):211-217. Some of the currently available anti-tubulin antibody preparations react with both sheep and pig brain tubulin and different types of tubulin are present within a trichomonad cell. However, actin isolated from *T. vaginalis* differs from that of pig and sheep skeletal muscle. Moreover, *T. vaginalis* actin was observed to migrate more slowly than actin isolated from muscle when purified by anion-exchange chromatography, and it was found to have different peptide sequences as indicated by cleavage with proteolytic enzymes. Id. Hence, these *Trichomonas* tubulin, and particularly actin, antigens can be used for making *Trichomonas*-specific antibodies.

An alpha-actin cDNA from *T. vaginalis* has been cloned, permitting analysis of conserved and unique peptide sequences within the *T. vaginalis* alpha-actin molecule and development of *Trichomonas*-specific antibodies. See Fillipa et al., *Cloning and Molecular Characterization of a cDNA Clone Coding for Trichomonas vaginalis Alpha-Actinin and Intracellular Localization of the Protein*, Infection and Immunity 66(10): 4924-31.

Thus, for example, one sequence for a *T. vaginalis* alpha-actinin protein is as follows (SEQ ID NO: 1).

```
  1  NSARGREGLL DDAWEKTQIK VFSRWVQKQL LARQIQFETI
 41  ETDFEDGTKL LNLLEIIGKE PMPGKWHKQP KMMVQKRETV
 81  DIALKYINEV KKIRTVGIGA DDIINKNLKL TLGLTWTCIN
121  KFMIEEISVE EATARDALLL WAKKNTQGYE HVAVNNFTTS
161  WNTGLAFAAL INKFRPNLLD YSALDYNDHK GACEKAFAAC
201  KELGIYVYLD PEDVIDTTPD EKSVVTQVAE FFHFFASESK
241  IAAMADKIKR TVAIQKQIDE LKNTYIEDAK AAIEKMTVED
281  EKLKADDYEK TIPGIRGKLA SVISYNRDIR PEIVDHRAKA
321  MRSWAALVTK CKSGNRPIPE IPQGLEPEAL TNKFNEIEQT
361  STTRRDELTQ ELNDMIKKKV EDFMAKCMDI INKCDAIHEE
401  VKTIEGTTAE KKDKVEQKLH EAEDLQPALA ELTPLFQELV
441  ELRINTLSSQ TDDSVNRHHS QLITYIKHLL EQLNGKLFEE
481  TNEARINEYN ALAQPLYDEA IAFKEEVLAI SGELRERRTQ
521  FLAKQAEAPT KREHVNEIDP IFDGLEKDSL HLRVNHSPTE
561  IRNVYAVTLQ HIITELNKIF EEMVANFDAT AVPIIDGITA
601  LVTSSHQIPG DAAAVKAQVE ENLASLDCVR RKDPSPPGSI
641  QRARSIQAQL IKVTYTYSDA TGELVQARLD LKQIILAKKT
681  FLEEEERKAR INNYTVKADE HMNEAHALDG KINSVDGELE
721  PKRQKLYEVR EEVNAKKEKA VEELTPIYED LEKDQLHLEI
761  TSTPASINIF FENLIAHIDT LVKEIDARIA AAKGLEISEE
801  ELNEFKDTFK YFDKDKSNSL EYFELKACLT ALGEDITDDQ
841  akeyckksl
```

The central portion of the *Trichomonas* alpha-actinin protein (amino acids 387 to 650) exhibits less homology with other actin and cytoskeletal proteins than do the N-terminal and C-terminal regions. See Fillipa et al., *Cloning and Molecular Characterization of a cDNA Clone Coding for Trichomonas vaginalis Alpha-Actinin and Intracellular Localization of the Protein*, Infection and Immunity 66(10): 4924-31. This central portion can be used as an antigen for generating *Trichomonas*-specific antibodies.

Hence, the invention contemplates using antibodies directed against the central portion of the *Trichomonas vaginalis* alpha-actinin protein, in particular, amino acids 387 to 650, in the devices, vaginal inserts and methods provided herein. For example, a polypeptide having the following non-conserved sequence provided below (SEQ ID NO:2) can be used to generate *Trichomonas*-specific antibodies.

```
387                             CMDI INKCDAIHEE
401  VKTIEGTTAE KKDKVEQKLH EAEDLQPALA ELTPLFQELV
441  ELRINTLSSQ TDDSVNRHHS QLITYIKHLL EQLNGKLFEE
```

```
481 TNEARINEYN ALAQPLYDEA IAFKEEVLAI SGELRERRTQ

521 FLAKQAEAPT KREHVNEIDP IFDGLEKDSL HLRVNHSPTE

561 IRNVYAVTLQ HIITELNKIF EEMVANFDAT AVPIIDGITA

601 LVTSSHQIPG DAAAVKAQVE ENLASLDCVR RKDPSPPGSI

641 QRARSIQAQL I
```

There are an estimated eight serotypes observed in *T. vaginalis*. Ackers, J. P. 1990. *Immunologic aspects of human trichomoniasis*, p. 36-52. In B. M. Honigberg (ed.), *Trichomonads parasitic in humans*. Springer-Verlag, New York, N.Y. However, by immunoblot analysis, a wide variety of antigenic markers are seen. Garber, G. E., L. T. Lemchuk-Favel, and W. R. Bowie. 1989. *Isolation of a cell-detaching factor of Trichomonas vaginalis*, J. Clin. Microbiol. 27:1548-1553. According to the invention, any of these antigenic markers can be used as *Trichomonas*-specific antigens.

*Trichomonas*-Specific Enzymes

As described above, the invention contemplates a device with a reporter enzyme linked to a core material by a linker, where the linker can be cleaved by a *Trichomonas*-specific enzyme to release the reporter enzyme for detection. One of skill in the art can use any available reporter enzyme and linker that can be cleaved by an enzyme specific to an infective agent.

Enzymes specific to *Trichomonas* include cysteine proteinases, phospholipase A2-like lytic enzymes, neuraminidases and the like.

For example, the following references describe cysteine proteinases that can be detected using the devices and methods of the invention: Leon-Sicairos et al., *tvcp12: a novel Trichomonas vaginalis cathepsin L-like cysteine proteinase-en coding gene*. Microbiology 150(5):1131-18 (May 2004); Leon-Sicairos et al., *Two Trichomonas vaginalis loci encoding for distinct cysteine proteinases show a genomic linkage with putative inositol hexakisphosphate kinase (IP6K2) or an ABC transporter gene*. J. Eukaryot. Microbiol. 50 Suppl.: 702-05 (2003); Hernandez-Gutierrez et al., *A 39-kDa cysteine proteinase CP39 from Trichomonas vaginalis, which is negatively affected by iron may be involved in trichomonal cytotoxicity*, J. Eukaryot. Microbiol. 50 Suppl: 696-8 (2003); Mendoza-Lopez et al. CP30, *a cysteine proteinase involved in Trichomonas vaginalis cytoadherence*, Infect. Immun. 68(9): 4907-12 (September 2000); Alvarez-Sanchez et al., *A novel cysteine proteinase (CP65) of Trichomonas vaginalis involved in cytotoxicity*, Microb. Pathog. 28(4):193-202 (April 2000); Min et al., *Degradations of human immunoglobulins and hemoglobin by a 60 kDa cysteine proteinase of Trichomonas vaginalis*, Korean J Parasitol. 36(4): 261-68 (December 1998); Draper et al., *Cysteine proteases of Trichomonas vaginalis degrade secretory leukocyte protease inhibitor*, J. Infect. Dis. 178(3): 815-19 (September 1998); Alderete et al., *The vagina has reducing environment sufficient for activation of Trichomonas vaginalis cysteine proteinases*, Genitourin. Med. 73(4):291-96 (August 1997); Irvine et al., *Use of inhibitors to identify essential cysteine proteinases of Trichomonas vaginalis*, FEMS Microbiol Lett. 149(1):45-50 (April 1997); Provenzano et al., *Analysis of human immunoglobulin-degrading cysteine proteinases of Trichomonas vaginalis*, Infect Immun. 63(9):3388-95 (September 1995); Arroyo et al., *Two Trichomonas vaginalis surface proteinases bind to host epithelial cells and are related to levels of cytoadherence and cytotoxicity*, Arch Med Res. 26(3):279-85 (1995); Mallinson et al., *Identification and molecular cloning off our cysteine proteinase genes from the pathogenic protozoon Trichomonas vaginalis*, Microbiology. 140(10): 2725-35 (October 1994); Garber et al., *Analysis of the extracellular proteases of Trichomonas vaginalis*, Parasitol Res. 80(5): 361-65 (1994); Irvine et al., *Purification of cysteine proteinases from trichomonads using bacitracin-Sepharose*, FEMS Microbiol Lett. 110(1) 113-9 (Jun. 1, 1993); Alderete et al., *The vagina of women infected with Trichomonas vaginalis has numerous proteinases and antibody to trichomonad proteinases*, Genitourin. Med. 67(6): 469-74 (December 1991); Bozner et al., *Proteinases in Trichomonas vaginalis and Trichomonas mobilensis are not exclusively of cysteine type, Parasitology*, 102(1): 113-15 (February 1991); North et al., *The specificity of trichomonad cysteine proteinases analysed using fluorogenic substrates and specific inhibitors*, Mol. Biochem. Parasitol. 39(2):183-93 (March 1990).

Such cysteine proteinases can be detected by cleavage of a linker between the reporter enzyme and the core material or membrane covering the core material. The linker can contain a cleavage site for the proteinase. For example, cysteine proteinases of *Trichomonas vaginalis* and *Trichomonas foetus* can cleave a variety of peptidyl linkers. Three general types of proteinases are found in *Trichomonas vaginalis*:

(1) an 86-kDa enzyme active on peptidyl substrates having an Arg-Arg cleavage site;
(2) a 54-kDa proteinase active on peptidyl substrates having a Phe-Arg cleavage site, a Val-Leu-Lys cleavage site, a Ala-Phe-Lys cleavage sit, a Pro-Phe-Arg cleavage site or an Arg-Arg cleavage site; and
(3) a group of six enzymes that preferentially hydrolyze peptidyl substrates with bulky residues at the P2 and P3 positions. Examples of cleavage sites for these enzymes include Val-Leu-Lys and Leu-Val-Tyr cleavage sites.

The proteinases of *Trichomonas foetus* had slightly different substrate specificity. All *Trichomonas foetus* proteinases are active on peptidyl substrates with Arg-Arg cleavage sites, but their activity towards other substrates varies. Three predominantly extracellular *Trichomonas foetus* proteinases (25, 27 and 34 kDa), hydrolyze peptidyl substrates with Arg-Arg cleavage sites. Other proteinases (apparent molecular weights of 20,000 and 32,000) hydrolyze a number of other substrates, with the 32-kDa enzyme having greater activity towards peptidyl substrates with Val-Leu-Lys or Leu-Val-Tyr cleavage sites than towards peptidyl substrates with Arg-Arg cleavage sites.

Hence, the proteinases of the two *Trichomonas* species are heterogeneous group with respect to specificity, and the presence of *Trichomonas vaginalis* and *Trichomonas foetus* can be distinguished based on their different substrate specificities. See North et al., *The specificity of trichomonad cysteine proteinases analysed using fluorogenic substrates and specific inhibitors*, Mol. Biochem. Parasitol. 39(2):183-93 (March 1990).

Other *Trichomonas* enzymes can be detected using different types of linkers between the core/membrane and the reporter enzyme. For example, *Trichomonas* enzymes that can be detected include phospholipase A2-like enzymes. Such enzymes have been described by the following: Lubick et al., *Purification and analysis of a phospholipase A2-like lytic factor of Trichomonas vaginalis*, Infect. Immun. 72(3): 1284-90 (March 2004); Vargas-Villarreal et al., *Trichomonas vaginalis: identification of a phospholipase A-dependent hemolytic activity in a vesicular subcellular fraction*, J. Parasitol. 89(1): 105-12 (February 2003); McGregor et al., *Association of cervicovaginal infections with increased vagi-*

*nal fluid phospholipase A2 activity*, Am. J. Obstet. Gynecol. 167(6):1588-94 (December 1992).

Phospholipases found in *Trichomonas* can be detected by incorporating a phosphoglycerides-like structure into a linker between the reporter enzyme and the core/membrane of the device. For example, an ester of the following structure can be used in the linker to detect phospholipase A activity:

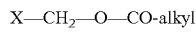

X—CH$_2$—O—CO-alkyl wherein X is a alkylene or triglyceride. In this embodiment, the linker can be an alkylene chain with the ester shown above as a phospholipase cleavage site.

Moreover, *Trichomonas vaginalis* and *Trichomonas foetus* secrete neuraminidase, which can be detected by cleavage of a linker containing a substrate specific to neuraminidase: 2'-(4-methylumbelliferyl)-alpha-D-N-acetylneuramic acid. See, Costa e Silva Filho et al., *Trichomonas vaginalis and Trichomonas foetus secrete neuraminidase into the culture medium*, Mol. Biochem. Parasitol. 35(1):73-78 (Jun. 1, 1989).

Hence, the device of the invention can include a reporter enzyme attached to the devices of the invention by a number of different linkers. Each linker can have a cleavage site that can be recognized and cleaved by a *Trichomonas*-specific enzyme, as described above.

Vaginal Insert

The invention relates to a vaginal insert or tampon that provides a detectable signal if *Trichomonas* are present. The vaginal insert includes an absorbent or non-absorbent core material compressed into a generally cylindrical shape. The core material can be covered by a membrane. Antibodies specific for an infective agent such as *Trichomonas* can be bound to the core material or to the membrane. Similarly, reporter enzymes are bound to the core material or to the membrane that can be cleaved from the core material or membrane by an enzyme specific for an infective agent.

The membrane can be any convenient membrane available to one of skill in the art to which antibodies, enzymes and proteins can be bound. Examples of membranes that can be used include nylon, nitrocellulose, polytetrafluoroethylene, or polyester membranes. Membrane covers can also be formed from woven or nonwoven materials having a porous substrate. Woven materials include textile fabrics and nonwoven materials include spunbond and bonded carded webs. Both of these nonwoven materials are commercially sold by Kimberly-Clark Corporation, 401 N. Lake Street, Neenah, Wis. 54956. Another nonwoven material which can be used as the membrane is formed from 100 percent polyester fibers held together by a binder. This material is known as powder-bonded-carded web (PBCW) and is also available from Kimberly-Clark Corporation.

In some embodiments, the covalent bond between the antibody or enzyme and the membrane or linker is a peptide bond. In other embodiments, the antibody or enzyme is attached to the core material or the membrane by a linker, for example, a peptidyl or alkyl linker.

Peptide bonds between antibodies or enzymes and a linker, membrane or core material can be formed selectively either between the N terminal of the antibody/enzyme and a selected carboxylate group on the linker, membrane or core material. Alternatively, the peptide bond can be formed selectively between the C terminal of the antibody/enzyme and an amino group of the linker, membrane or core material. If a selected region of the antibody/enzyme is to be linked to the linker, membrane or core material, such selective interaction can be controlled by blocking the N terminal or the C terminal of the antibody/enzyme so that the selected reactive groups form a linkage. Similarly, blocking groups on the amino or carboxylate groups of the linker/membrane can be used to guide linkage of the antibodies/enzymes to the desired location.

The use of chemical protective groups for the region-specific bond formation is familiar to the person skilled in the art. Thus, for example, with respect to the antibody/enzyme, a protection of an N-terminal amino group can be achieved by introducing a tert-butoxycarbonyl group (Boc). Subsequent to the reaction with the linker, membrane or core material, the Boc group can be removed from the amino group by hydrolysis. With respect to the linker, the coupling of the antibody/enzyme can be controlled by use of linkers without reactive groups or by protection of such reactive groups with protecting groups available in the art.

Figure 2:
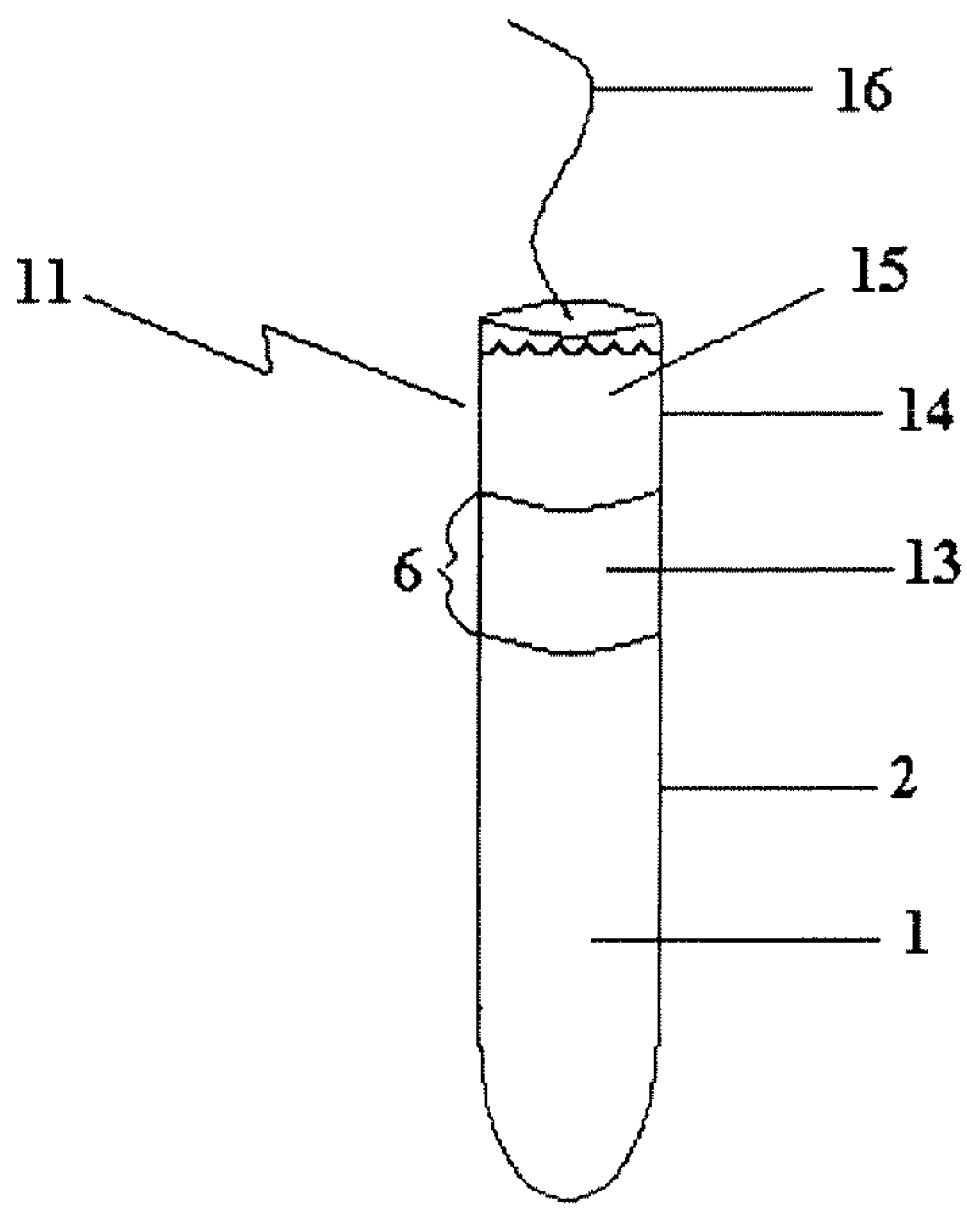
FIG. 2 provides a diagnostic device for detecting an antigen from an infective organism, for example, *Trichomonas*. The diagnostic device includes a vaginal insert to sample the vaginal flora. The diagnostic device is made up of several parts: a solid support core (1); a membrane (2), such as but not limited to nitrocellulose, that covers the core (1); primary antibodies (13) that can bind to one or more surface antigens of the infective organism (e.g. *Trichomonas*) and that have been immobilized on the exterior surface membrane of the diagnostic device; a compartment (14) containing fluid with secondary antibodies (15) for detecting the antigen, wherein the compartment (14) ruptures when squeezed. The primary antibodies (13) and secondary antibodies (15) can bind to the same or to different surface antigens of the infective organism (e.g. *Trichomonas*). However, the secondary antibodies (15) are conjugated to a detectable (e.g. visible) label. The primary antibodies (13) are immobilized onto a zone (6) on the exterior surface membrane of the diagnostic device. The device is inserted into the vagina and retained therein for a time sufficient to permit reaction between the primary antibody (13) and the antigen(s) of the infective organism. The device is then removed from the vagina. The compartment (14) is then ruptured by squeezing to release the fluid containing the secondary antibodies (15). If antigen(s) of the infective organism are present, the antigen(s) will bind to the primary antibodies (13) and then to the secondary antibodies (15). The device can be washed in a convenient fluid (e.g. water in a towel bowl) or under the faucet to ascertain whether the detectable label remains associated with the zone (6). In some embodiments, the secondary antibodies (15) are linked to a detectable label that can react with a color indicator (5) as shown in FIG. 1 to change the color of the zone (6).

Referring to FIGS. 1-2, the device includes an absorbent or non-absorbent core 1 that has been rolled, formed or compressed into a generally cylindrical shape. A membrane can be placed around the device by positioning the core material 1 on the membrane 2, and then rolling the two layers into a generally cylindrical shape. This uncompressed cylindrical shape is known as a "softwind." The softwind can be further compressed into a more compact shape if needed. It should be noted that it is also possible to first form the core material 1 into a generally cylindrical shape and then wrap the membrane 2 around it. It is also possible to roll up, form and/or compress the core material 1 before wrapping it in the membrane 2.

Referring to FIG. 1-2, the device further includes a withdrawal string 16 that is secured to either the core material 1, the membrane 2 or to both and provides a safe and reliable means by which the device can be withdrawn from a female vagina. The withdrawal string 16 can be incorporated during formation of the core material 1 into a cylinder, or during attachment of the membrane 2. Alternatively, the string 16 can be attached to the fully formed core 1, depending upon one's preference. In any of these cases, the free end of the withdrawal string 16 can be tied into a knot 18 to assure that the string 16 will not be separated from the core 1 or the membrane 2.

The core material 1 can be an absorbent material. Such an absorbent material can be formed from absorbent fibers that are first assembled into an absorbent ribbon or sheet. Alternatively, the absorbent material can be formed from absorbent fibers that are assembled and compressed into a generally cylindrical configuration. The absorbent material can be formed from cellulosic fibers, such as cotton and rayon. The absorbent material can be 100% cotton, 100% rayon, or a blend of both cotton and rayon. A ratio of from about 15% cotton and about 85% rayon works well. The particular blend of fibers can vary depending on one's preference.

The cotton fibers should have a staple length of between about 5 mm to about 20 mm. The fibers can be bleached if desired. Bleaching will make the fibers whiter in appearance. The cotton should generally have a fiber size of between about 150 to about 280 microns.

The rayon fibers should have a staple length of between about 20 mm to about 35 mm. The fibers can also be bleached if desired. The rayon fibers should have a denier of between about 25 to about 28. Denier is a unit of fineness of yarn based on a standard of 50 milligrams per 450 meters of yarn.

The absorbent material formed from an absorbent ribbon is typically constructed from a blend of rayon and cotton fibers in a process known to those skilled in the art as "carding." Depending upon the desired absorbency one desires in the finished device, the basis weight of the absorbent ribbon can vary.

The membrane 2 can be bonded to the core 1 using heat, pressure or a combination of heat and pressure. In some embodiments, the bonding will occur during the compression step.

The withdrawal string 16 can be constructed from various types of threads or ribbons. A thread made from 100 percent cotton fibers works well. The withdrawal string 16 extends beyond one end of the device for a distance of about 2 inches to about 8 inches (about 50.8 mm to about 203.2 mm), or from about 4 inches to about 6 inches (about 102 mm to about 152.4 mm), or for about 5 inches (127 mm). The withdrawal string 16 can be dyed and/or treated with an anti-wicking agent, such as wax, before being secured to the core or softwind to prevent it from wicking vaginal fluid. A dry, clean withdrawal string 16 is preferred by the user for removal of the device.

Methods

In one aspect, the invention includes a method for detecting *Trichomonas* infection in a human subject. In practicing the method, a device of the invention is inserted into a female vagina for a time sufficient for interaction between an infective agent (or an enzyme specific to the infective agent) and the reporter enzymes (3) or the primary antibody (13) and the antigen(s) of the infective organism.

The time sufficient for interaction between an infective agent (or an enzyme specific to the infective agent) and the reporter enzymes (3), or between the antigen(s) specific to the infective agent and the primary antibody (13) can vary. For example, such a time can range from about 5 seconds to about 2 hours, or from about 10 seconds to about 90 minutes, or from about 30 seconds to about 1 hour.

The device is then removed. To detect the presence of *Trichomonas*-specific enzymes, the device is then dipped several times in a solution containing a color indicator (5). Such dipping washes any reporter enzyme from the device that has been cleaved from the device by the *Trichomonas*-specific enzymes. After dipping the device several times, it is removed and can be discarded. The color indicator (5) changes color, or develops color, if the reporter enzymes (3) are present. Hence, if the infective agent is present, some of the reporter enzymes (3) will be cleaved from the absorbent core (1) and be washed into the color indicator (5) solution where the liberated reporter enzymes will cause the color indicator (5) to change color, or to develop a colored solution.

The time and conditions needed for detection of a change in color or a development of color by the reporter enzymes (3) can vary and depends to some extent upon the type of reporter enzymes (3) and color indicator (5) solution employed. Typically, the color indicator (5) contains a fluorometric, luminescent or calorimetric substrate for an enzyme. Many such fluorometric, luminescent or calorimetric substrates are available from Sigma (St. Louis, Mo.). Many enzymes, such as beta-lactamase, alkaline phosphatase, luciferase, and beta-galactosidase have been used as reporter enzymes to monitor biological events. See, Moore, et al., (1997) Annal. Biochem. 247: 203; Chubb, A. J. et al. (1998) Microbiology 144, 1619; Chen, H. and Leder, P. (1999) Nucleic Acids Research, 27, 1219; U.S. Pat. Nos. 5,801,000, and 5,554,499; Zlokarnik, G. et al., (1998) Science 279, 84; and Raz, E. et al., (1998) Development Biology 203 290.

The invention also provides a method for diagnosing *Trichomonas* by detecting an antigen from *Trichomonas* using a diagnostic device of the invention. In this embodiment, the diagnostic device has a solid support core (1), a membrane (2) that covers the core (1), primary antibodies (13) that can bind to one or more surface antigens of the infective organism (e.g. *Trichomonas*) and that have been immobilized on the exterior surface membrane of the diagnostic device, and a compartment (14) containing fluid with secondary antibodies (15) for detecting the antigen when the compartment (14) is ruptured by squeezing. See FIG. 2. The primary antibodies (13) are immobilized onto a zone (6) on the exterior surface membrane of the diagnostic device. The primary antibodies (13) and secondary antibodies (15) can bind to the same or to different surface antigens of the infective organism (e.g. *Trichomonas*), but the secondary antibodies (15) are conjugated to a detectable (e.g. visible) label.

This method involves inserting a device of the invention into a vagina of a mammal and retaining the device therein for a time sufficient to permit reaction between the primary antibody (13) and the antigen(s) of the infective organism (e.g. *Trichomonas*). The device is then removed from the vagina and the compartment (14) in the device is ruptured by squeezing to release the fluid containing the secondary antibodies (15). If antigen(s) of the infective organism are present, the antigen(s) will bind to the primary antibodies (13) and then to the secondary antibodies (15). The device can be washed in a convenient fluid (e.g. water in a towel bowl) or under the faucet to ascertain whether the detectable label remains associated with the zone (6). In some embodiments, the secondary antibodies (15) are linked to a detectable label that can react with a color indicator (5) as shown in FIG. 1 to change the color of the zone (6).

The presence or absence of the infective organism (e.g. *Trichomonas*) is detected with a reliability of at least about 80%, and typically at least about than 90% with any of the methods of the invention.

The devices and methods of the invention are applicable to detect *Trichomonas* in mammals, including humans, zoo animals and domesticated animals. Domesticated and zoo animals include cattle, horses, pigs, goats, monkeys, and other animals typically kept in zoos, farms and private residences. For example, *Trichomonas foetus* infection can be detected in cows using antibodies directed against *Trichomonas vaginalis* or *Trichomonas foetus* antigens. Alternatively, the devices of the invention can be used that have linker cleavage sites that can be cleaved by *Trichomonas vaginalis* or *Trichomonas foetus* enzymes.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for detecting *Trichomonas* in a vagina of a female mammal that comprises:
   inserting a diagnostic device into a test subject's vagina, the diagnostic device including a core and a reporter enzyme that is linked directly or indirectly to the core by a linker, the linker being a polypeptide comprising a cleavage site selected from the group consisting of an Arg-Arg cleavage site, a Phe-Arg cleavage site, a Val-Leu-Lys cleavage site, a Ala-Phe-Lys cleavage site, a Pro-Phe-Arg cleavage site, and a Leu-Val-Tyr cleavage site, or the linker being an ester of the structure:

X—CH$_2$—O—CO-alkyl wherein X is an alkylene or a triglyceride, or the linker being 2'-(4-methylumbelliferyl)-alpha-D-N-acetyl-neuramic acid,
   retaining the device in the vagina for a time sufficient for reaction of a *Trichomonas*-specific enzyme with the linker, the *Trichomonas*-specific enzyme cleaving the linker and releasing the reporter enzyme,
   removing the device from the test subject's vagina, and
   dipping the device into a solution containing a substrate for the reporter enzyme to detect *Trichomonas* in the vagina of the test subject.

2. The method of claim 1, wherein the substrate is a fluorometric, luminescent, or calorimetric substrate for the reporter enzyme.

3. The method of claim 1, wherein interaction between the reporter enzyme and the substrate for the reporter enzyme gives rise to a colored product.

4. The method of claim 1, wherein the reporter enzyme is beta-lactamase, alkaline phosphatase, luciferase, or beta-galactosidase.

5. The method of claim 1, wherein the method detects *Trichomonas vaginalis*.

6. The method of claim 1, wherein the method detects *Trichomonas foetus*.

7. The method of claim 1, wherein the *Trichomonas*-specific enzyme is a proteinase.

8. The method of claim 1, wherein the *Trichomonas*-specific enzyme is a phospholipase A2-like enzyme.

9. The method of claim 1, wherein the *Trichomonas*-specific enzyme is a neuraminidase.

* * * * *

SEQUENCE LISTING

```
<160> NUMBER OF SEQ ID NOS: 2

<210> SEQ ID NO 1
<211> LENGTH: 849
<212> TYPE: PRT
<213> ORGANISM: Trichomonas vaginalis

<400> SEQUENCE: 1

Asn Ser Ala Arg Gly Arg Glu Gly Leu Leu Asp Asp Ala Trp Glu Lys
 1               5                  10                  15

Thr Gln Ile Lys Val Phe Ser Arg Trp Val Gln Lys Gln Leu Leu Ala
            20                  25                  30

Arg Gln Ile Gln Phe Glu Thr Ile Glu Thr Asp Phe Glu Asp Gly Thr
        35                  40                  45

Lys Leu Leu Asn Leu Leu Glu Ile Ile Gly Lys Glu Pro Met Pro Gly
    50                  55                  60

Lys Trp His Lys Gln Pro Lys Met Met Val Gln Lys Arg Glu Thr Val
65                  70                  75                  80

Asp Ile Ala Leu Lys Tyr Ile Asn Glu Val Lys Lys Ile Arg Thr Val
                85                  90                  95

Gly Ile Gly Ala Asp Asp Ile Ile Asn Lys Asn Leu Lys Leu Thr Leu
            100                 105                 110

Gly Leu Thr Trp Thr Cys Ile Asn Lys Phe Met Ile Glu Glu Ile Ser
        115                 120                 125

Val Glu Glu Ala Thr Ala Arg Asp Ala Leu Leu Leu Trp Ala Lys Lys
    130                 135                 140

Asn Thr Gln Gly Tyr Glu His Val Ala Val Asn Asn Phe Thr Thr Ser
145                 150                 155                 160

Trp Asn Thr Gly Leu Ala Phe Ala Ala Leu Ile Asn Lys Phe Arg Pro
                165                 170                 175

Asn Leu Leu Asp Tyr Ser Ala Leu Asp Tyr Asn Asp His Lys Gly Ala
            180                 185                 190

Cys Glu Lys Ala Phe Ala Ala Cys Lys Glu Leu Gly Ile Tyr Val Tyr
        195                 200                 205

Leu Asp Pro Glu Asp Val Ile Asp Thr Thr Pro Asp Glu Lys Ser Val
    210                 215                 220

Val Thr Gln Val Ala Glu Phe Phe His Phe Phe Ala Ser Glu Ser Lys
```

```
                225                 230                 235                 240
Ile Ala Ala Met Ala Asp Lys Ile Lys Arg Thr Val Ala Ile Gln Lys
                245                 250                 255
Gln Ile Asp Glu Leu Lys Asn Thr Tyr Ile Glu Asp Ala Lys Ala Ala
                260                 265                 270
Ile Glu Lys Met Thr Val Glu Asp Lys Leu Lys Ala Asp Asp Tyr
                275                 280                 285
Glu Lys Thr Ile Pro Gly Ile Arg Gly Lys Leu Ala Ser Val Ile Ser
    290                 295                 300
Tyr Asn Arg Asp Ile Arg Pro Glu Ile Val Asp His Arg Ala Lys Ala
305                 310                 315                 320
Met Arg Ser Trp Ala Ala Leu Val Thr Lys Cys Lys Ser Gly Asn Arg
                325                 330                 335
Pro Ile Pro Glu Ile Pro Gln Gly Leu Glu Pro Glu Ala Leu Thr Asn
                340                 345                 350
Lys Phe Asn Glu Ile Glu Gln Thr Ser Thr Thr Arg Arg Asp Glu Leu
                355                 360                 365
Thr Gln Glu Leu Asn Asp Met Ile Lys Lys Val Glu Asp Phe Met
    370                 375                 380
Ala Lys Cys Met Asp Ile Ile Asn Lys Cys Asp Ala Ile His Glu Glu
385                 390                 395                 400
Val Lys Thr Ile Glu Gly Thr Thr Ala Glu Lys Lys Asp Lys Val Glu
                405                 410                 415
Gln Lys Leu His Glu Ala Glu Asp Leu Gln Pro Ala Leu Ala Glu Leu
                420                 425                 430
Thr Pro Leu Phe Gln Glu Leu Val Glu Leu Arg Ile Asn Thr Leu Ser
                435                 440                 445
Ser Gln Thr Asp Asp Ser Val Asn Arg His His Ser Gln Leu Ile Thr
    450                 455                 460
Tyr Ile Lys His Leu Leu Glu Gln Leu Asn Gly Lys Leu Phe Glu Glu
465                 470                 475                 480
Thr Asn Glu Ala Arg Ile Asn Glu Tyr Asn Ala Leu Ala Gln Pro Leu
                485                 490                 495
Tyr Asp Glu Ala Ile Ala Phe Lys Glu Glu Val Leu Ala Ile Ser Gly
                500                 505                 510
Glu Leu Arg Glu Arg Thr Gln Phe Leu Ala Lys Gln Ala Glu Ala
                515                 520                 525
Pro Thr Lys Arg Glu His Val Asn Glu Ile Asp Pro Ile Phe Asp Gly
                530                 535                 540
Leu Glu Lys Asp Ser Leu His Leu Arg Val Asn His Ser Pro Thr Glu
545                 550                 555                 560
Ile Arg Asn Val Tyr Ala Val Thr Leu Gln His Ile Ile Thr Glu Leu
                565                 570                 575
Asn Lys Ile Phe Glu Glu Met Val Ala Asn Phe Asp Ala Thr Ala Val
                580                 585                 590
Pro Ile Ile Asp Gly Ile Thr Ala Leu Val Thr Ser Ser His Gln Ile
                595                 600                 605
Pro Gly Asp Ala Ala Val Lys Ala Gln Val Glu Glu Asn Leu Ala
    610                 615                 620
Ser Leu Asp Cys Val Arg Arg Lys Asp Pro Ser Pro Gly Ser Ile
625                 630                 635                 640
Gln Arg Ala Arg Ser Ile Gln Ala Gln Leu Ile Lys Val Thr Tyr Thr
                645                 650                 655
```

```
Tyr Ser Asp Ala Thr Gly Glu Leu Val Gln Ala Arg Leu Asp Leu Lys
        660                 665                 670

Gln Ile Ile Leu Ala Lys Lys Thr Phe Leu Glu Glu Glu Arg Lys
    675                 680                 685

Ala Arg Ile Asn Asn Tyr Thr Val Lys Ala Asp Glu His Met Asn Glu
    690                 695                 700

Ala His Ala Leu Asp Gly Lys Ile Asn Ser Val Asp Gly Glu Leu Glu
705                 710                 715                 720

Pro Lys Arg Gln Lys Leu Tyr Glu Val Arg Glu Val Asn Ala Lys
                725                 730                 735

Lys Glu Lys Ala Val Glu Glu Leu Thr Pro Ile Tyr Glu Asp Leu Glu
            740                 745                 750

Lys Asp Gln Leu His Leu Glu Ile Thr Ser Thr Pro Ala Ser Ile Asn
        755                 760                 765

Ile Phe Phe Glu Asn Leu Ile Ala His Ile Asp Thr Leu Val Lys Glu
    770                 775                 780

Ile Asp Ala Arg Ile Ala Ala Lys Gly Leu Glu Ile Ser Glu Glu
785                 790                 795                 800

Glu Leu Asn Glu Phe Lys Asp Thr Phe Lys Tyr Phe Asp Lys Asp Lys
                805                 810                 815

Ser Asn Ser Leu Glu Tyr Phe Glu Leu Lys Ala Cys Leu Thr Ala Leu
            820                 825                 830

Gly Glu Asp Ile Thr Asp Asp Gln Ala Lys Glu Tyr Cys Lys Lys Ser
        835                 840                 845

Leu

<210> SEQ ID NO 2
<211> LENGTH: 265
<212> TYPE: PRT
<213> ORGANISM: Trichomonas vaginalis

<400> SEQUENCE: 2

Cys Met Asp Ile Ile Asn Lys Cys Asp Ala Ile His Glu Glu Val Lys
1               5                   10                  15

Thr Ile Glu Gly Thr Thr Ala Glu Lys Lys Asp Lys Val Glu Gln Lys
            20                  25                  30

Leu His Glu Ala Glu Asp Leu Gln Pro Ala Leu Ala Glu Leu Thr Pro
        35                  40                  45

Leu Phe Gln Glu Leu Val Glu Leu Arg Ile Asn Thr Leu Ser Ser Gln
    50                  55                  60

Thr Asp Asp Ser Val Asn Arg His Ser Gln Leu Ile Thr Tyr Ile
65                  70                  75                  80

Lys His Leu Leu Glu Gln Leu Asn Gly Lys Leu Phe Glu Glu Thr Asn
                85                  90                  95

Glu Ala Arg Ile Asn Glu Tyr Asn Ala Leu Ala Gln Pro Leu Tyr Asp
            100                 105                 110

Glu Ala Ile Ala Phe Lys Glu Glu Val Leu Ala Ile Ser Gly Glu Leu
        115                 120                 125

Arg Glu Arg Arg Thr Gln Phe Leu Ala Lys Gln Ala Glu Ala Pro Thr
    130                 135                 140

Lys Arg Glu His Val Asn Glu Ile Asp Pro Ile Phe Asp Gly Leu Glu
145                 150                 155                 160

Lys Asp Ser Leu His Leu Arg Val Asn His Ser Pro Thr Glu Ile Arg
                165                 170                 175

Asn Val Tyr Ala Val Thr Leu Gln His Ile Ile Thr Glu Leu Asn Lys
```

-continued

```
                    180                 185                 190
Ile Phe Glu Glu Met Val Ala Asn Phe Asp Ala Thr Ala Val Pro Ile
        195                 200                 205

Ile Asp Gly Ile Thr Ala Leu Val Thr Ser Ser His Gln Ile Pro Gly
        210                 215                 220

Asp Ala Ala Ala Val Lys Ala Gln Val Glu Glu Asn Leu Ala Ser Leu
225                 230                 235                 240

Asp Cys Val Arg Arg Lys Asp Pro Ser Pro Pro Gly Ser Ile Gln Arg
                245                 250                 255

Ala Arg Ser Ile Gln Ala Gln Leu Ile
                260                 265
```